US006655381B2

United States Patent
Keane et al.

(10) Patent No.: US 6,655,381 B2
(45) Date of Patent: Dec. 2, 2003

(54) PRE-METERED DOSE MAGAZINE FOR BREATH-ACTUATED DRY POWDER INHALER

(75) Inventors: Laurence Keane, Aldwick (GB); David O'Leary, Essex (GB)

(73) Assignee: IVAX Corporation, Miami, FL (US)

( * ) Notice: Subject to any disclaimer, the term of this patent is extended or adjusted under 35 U.S.C. 154(b) by 0 days.

(21) Appl. No.: 09/888,277

(22) Filed: Jun. 23, 2001

(65) Prior Publication Data
US 2002/0073997 A1 Jun. 20, 2002

Related U.S. Application Data
(60) Provisional application No. 60/213,667, filed on Jun. 23, 2000, and provisional application No. 60/213,382, filed on Jun. 23, 2000.

(51) Int. Cl.[7] .............................................. A61M 15/00
(52) U.S. Cl. .............................. 128/203.15; 128/203.21
(58) Field of Search ..................... 128/203.15, 203.21, 128/200.19, 203.14, 200.23, 203.12, 203.18

(56) References Cited

U.S. PATENT DOCUMENTS

| | | | | |
|---|---|---|---|---|
| 4,627,432 A | * | 12/1986 | Newell et al. ......... | 128/200.19 |
| 4,668,218 A | | 5/1987 | Virtanen | |
| 5,035,237 A | * | 7/1991 | Newell et al. ......... | 128/203.15 |
| 5,388,572 A | | 2/1995 | Mulhauser et al. | |
| 5,458,135 A | | 10/1995 | Patton et al. | |
| 5,505,195 A | * | 4/1996 | Wolf et al. ............ | 128/200.23 |
| 5,529,059 A | | 6/1996 | Armstrong et al. | |
| 5,622,166 A | | 4/1997 | Eisele et al. | |
| 6,006,747 A | * | 12/1999 | Eisele et al. ........... | 128/203.15 |
| 6,065,472 A | * | 5/2000 | Anderson et al. ...... | 128/200.18 |
| 6,116,238 A | * | 9/2000 | Jackson et al. ........ | 128/203.12 |
| 6,273,085 B1 | * | 8/2001 | Eisele et al. ........... | 128/200.14 |
| 6,325,061 B1 | * | 12/2001 | Dagsland ............... | 128/203.12 |

FOREIGN PATENT DOCUMENTS

| | | |
|---|---|---|
| EP | 1129705 A1 | 9/2001 |
| EP | 525720 A1 | 2/2003 |
| GB | 2264237 A | 8/1993 |
| WO | WO 94/08552 | 4/1994 |
| WO | WO 99/36116 | 7/1999 |

* cited by examiner

Primary Examiner—William C. Doerrler
(74) Attorney, Agent, or Firm—McDermott, Will & Emery

(57) ABSTRACT

A pre-metered dose assembly for consistently supplying precise doses of medicament is provided for a breath-actuated dry powder inhaler. The assembly includes a cap defining a dry powder delivery passageway for providing air to a dry powder supply port of a swirl chamber of a breath-actuated dry powder inhaler, and a magazine including a plurality of reservoirs for holding pre-metered doses of dry powder. One of the magazine and the cap is movable with respect to the other of the magazine and the cap for sequentially positioning the reservoirs within the delivery passageway of the cap. A breath-induced low pressure at an outlet port of the swirl chamber of the inhaler causes an air flow through the dry powder delivery passageway of the assembly and into the dry powder supply port of the swirl chamber that entrains dry powder from the reservoir positioned in the passageway for inhalation by a patient using the inhaler. The present disclosure also provides a breath-actuated dry powder inhaler including the pre-metered dose assembly in combination with a de-agglomerator for breaking up aggregates and micronizing particles of dry powder prior to inhalation of the powder by a patient.

59 Claims, 6 Drawing Sheets

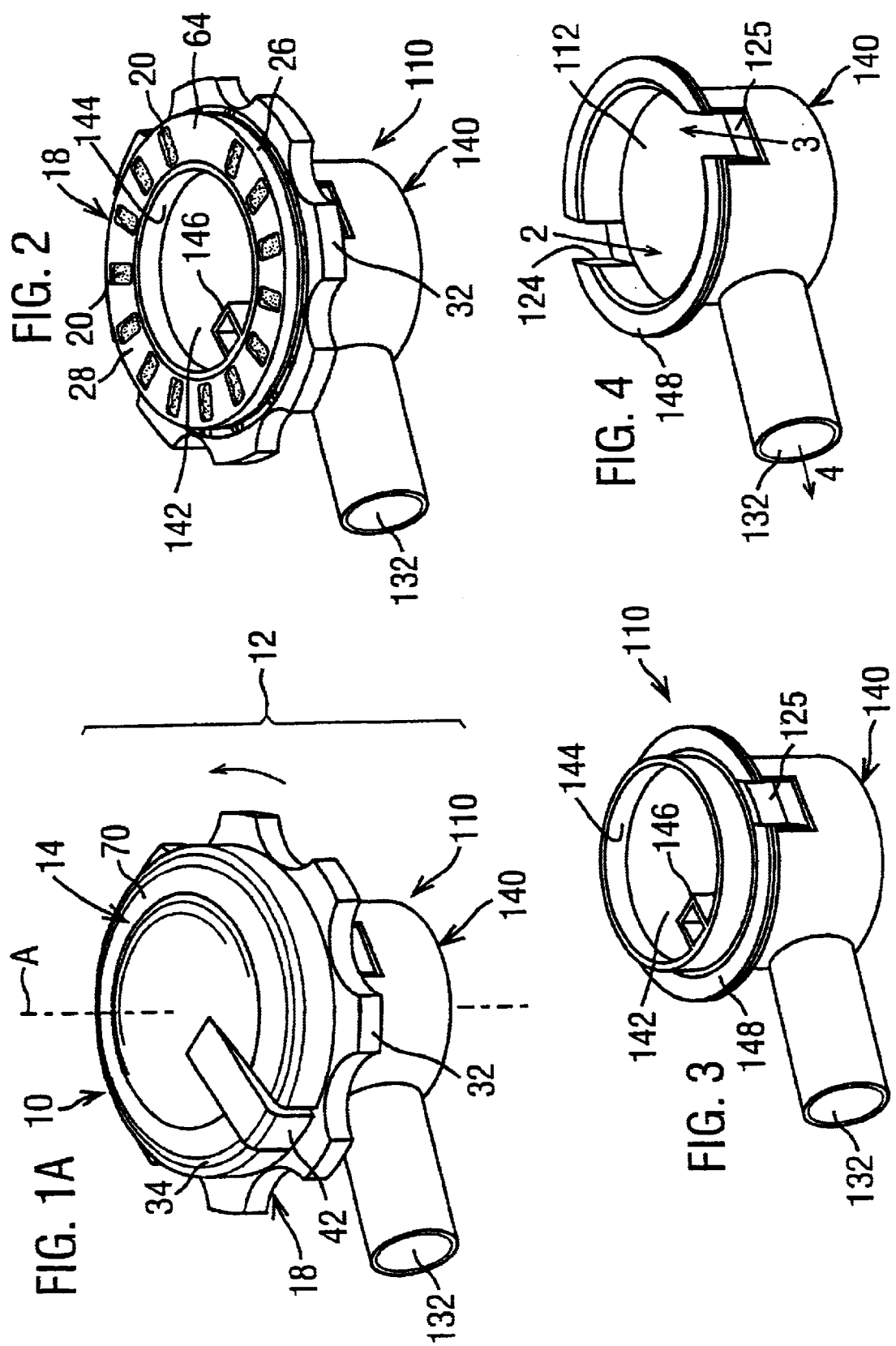

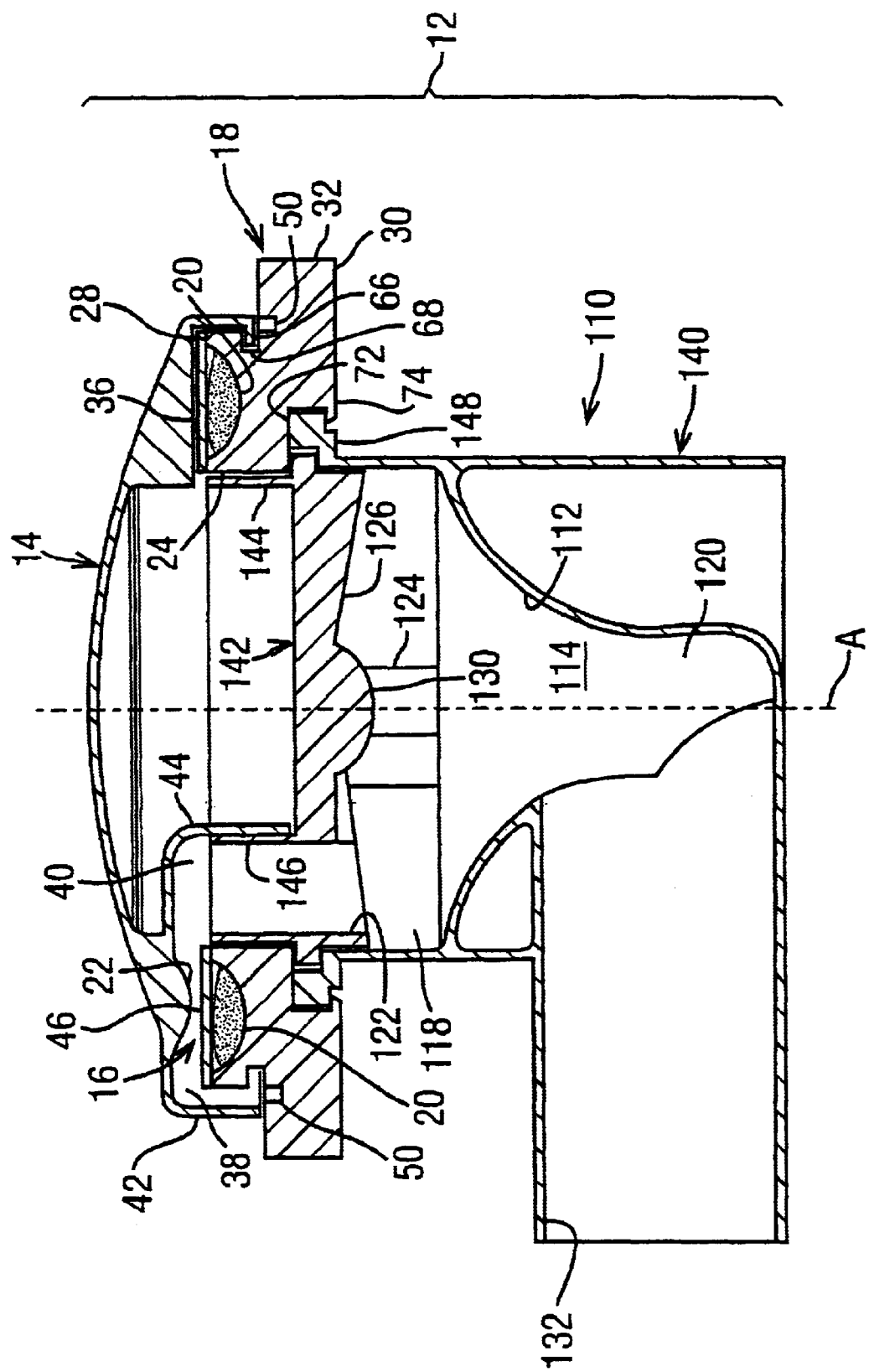

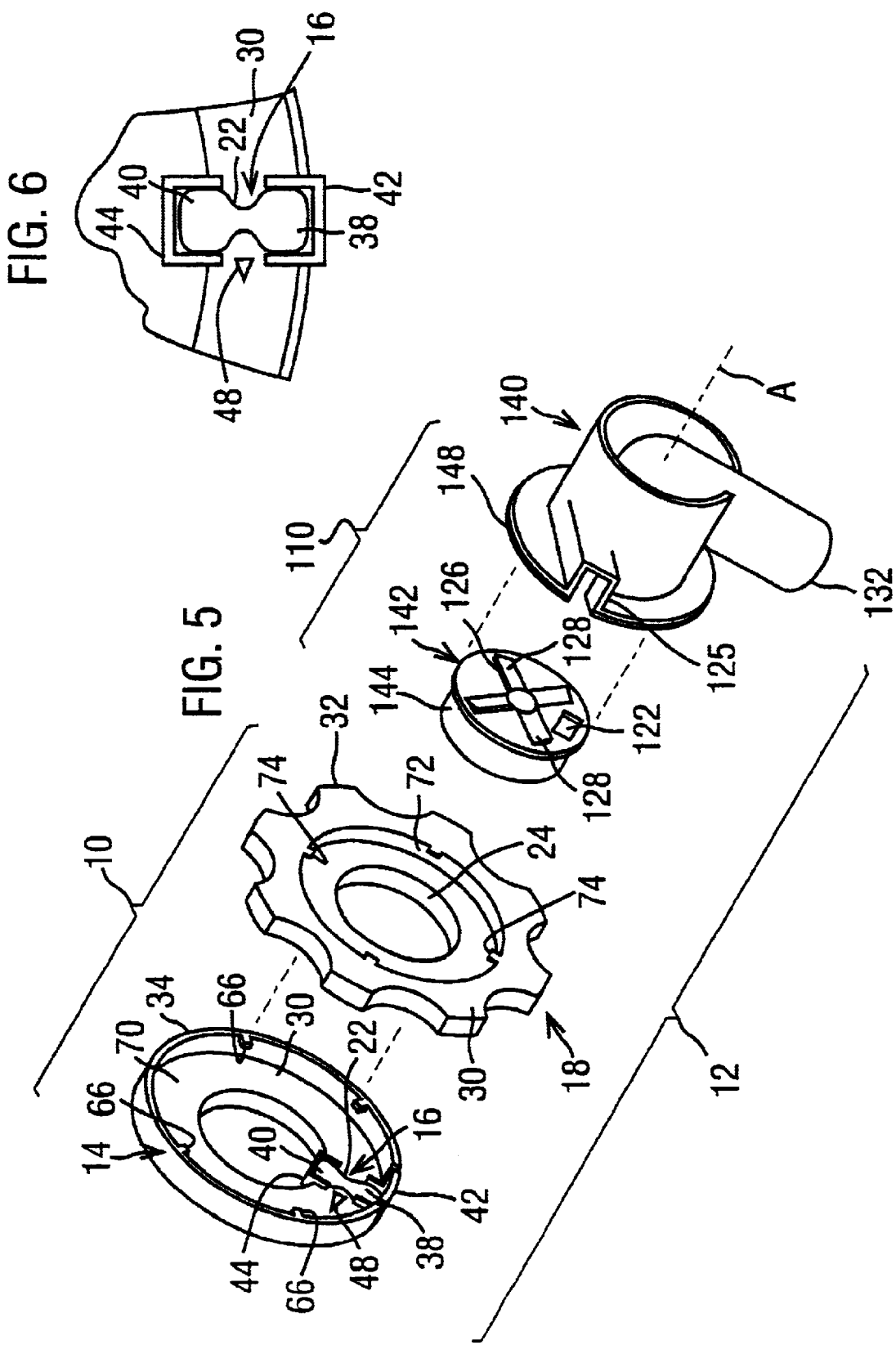

PRE-METERED DOSE MAGAZINE FOR BREATH-ACTUATED DRY POWDER INHALER

CROSS-REFERENCE TO RELATED APPLICATIONS

The present application claims priority to provisional U.S. patent application Ser. No. 60/213,667, filed Jun. 23, 2000 (entitled "Pre-Metered Dose Magazine for Breath-Actuated Dry Powder Inhaler"), and provisional U.S. patent application Ser. No. 60/213,382, filed Jun. 23, 2000 (entitled "De-Agglomerator for Breath-Actuated Dry Powder Inhaler"). Each of these co-pending applications is assigned to the assignee of the present disclosure and incorporated herein by reference.

FIELD OF THE INVENTION

The invention relates to a breath-actuated dry powder inhaler for administering dry powder medicament to a patient. More particularly, the present disclosure relates to a magazine having a plurality of individually separated, pre-metered doses for a breath-actuated dry powder inhaler and a method for providing pre-metered doses of dry powder medicament for inhalation by a patient.

BACKGROUND OF THE INVENTION

Metered dose medicament inhalers are well known for dispensing medicament to the lungs of a patient. In most cases, the inhalers include a reservoir containing dry powder medicament in bulk form, and means for metering the medicament from the reservoir in discrete amounts for inhalation by a patient.

For example, U.S. Pat. No. 5,503,144, which is assigned to the assignee of the present disclosure and incorporated herein by reference, shows a breath-actuated dry-powder inhaler having a medicament reservoir. The reservoir contains dry-powder medicament in bulk form, and the inhaler includes a metering chamber for removal of the powdered medicament from the reservoir in discrete amounts. The inhaler also includes an air inlet for entraining the removed powdered medicament through a mouthpiece upon patient inhalation.

While the reservoir and metering chamber of the inhaler shown by U.S. Pat. No. 5,503,144 properly function to dispense discrete amounts of powdered medicament to a patient, there is desired an inhaler having pre-metered doses of powdered medicament. Providing the powdered medicament in pre-metered doses will further ensure that the medicament is consistently dispensed to a patient in precise doses.

In particular, a device and method are desired for providing individually sealed, pre-metered doses of dry powder medicament for inhalation by a patient through a dry powder inhaler and, in particular, a breath-actuated, dry powder inhaler.

An improved breath-actuated, dry powder inhaler, which substantially de-agglomerates and micronizes pre-metered doses of medicament is also desired to ensure that particles of the medicament are small enough for adequate penetration of the medicament into a bronchial region of a patient's lungs during inhalation.

SUMMARY OF THE INVENTION

The present disclosure accordingly provides a pre-metered dose assembly for consistently supplying precise doses of medicament to a breath-actuated dry powder inhaler. The assembly includes a cap defining a dry powder delivery passageway for providing air to a dry powder supply port of a swirl chamber of a breath-actuated dry powder inhaler, and a magazine including a plurality of reservoirs for holding pre-metered doses of dry powder. One of the magazine and the cap is movable with respect to the other of the magazine and the cap for sequentially positioning the reservoirs within the delivery passageway of the cap. A breath-induced low pressure at an outlet port of the swirl chamber of the inhaler causes an air flow through the dry powder delivery passageway of the assembly and into the dry powder supply port of the swirl chamber. The air flow entrains dry powder from the reservoir positioned in the passageway for inhalation by a patient using the inhaler.

The present disclosure also provides a breath-actuated dry powder inhaler including the pre-metered dose assembly in combination with a de-agglomerator for breaking up aggregates and micronizing particles of dry powder prior to inhalation of the powder by a patient. The de-agglomerator includes an inner wall defining a swirl chamber extending along an axis from a first end to a second end, a dry powder supply port, one or more primary air flow inlet ports, and an outlet port. The supply port is at the first end of the swirl chamber for providing fluid communication between the dry powder delivery passageway of the pre-metered dose assembly and the first end of the swirl chamber. The primary air flow inlet ports are in the inner wall of the swirl chamber adjacent to or near the first end of the swirl chamber and provide fluid communication between a region exterior to the de-agglomerator and the swirl chamber. The outlet port provides fluid communication between the second end of the swirl chamber and a region exterior to the de-agglomerator.

A breath-induced low pressure at the outlet port of the de-agglomerator causes air flows into the swirl chamber through the dry powder supply port and the inlet port. The air flows collide with each other and with the wall of the swirl chamber prior to exiting through the outlet port, such that any powder entrained in the air flows is broken down and micronized. The de-agglomerator further includes vanes at the first end of the swirl chamber for creating additional collisions and impacts of entrained powder.

Further features and advantages of the presently disclosed pre-metered dose magazine and method for providing pre-metered doses will become more readily apparent to those having ordinary skill in the art to which the present disclosure relates from the following detailed description and attached drawings.

BRIEF DESCRIPTION OF THE DRAWINGS

So that those having ordinary skill in the art will more readily understand how to construct a pre-metered dose magazine and a breath-actuated, dry powder inhaler in accordance with the present disclosure, a preferred embodiments are described in detail below with reference to the drawing figures wherein:

FIG. 1A is a top isometric view of a breath-actuated, dry powder inhaler including a pre-metered dose magazine according to the present disclosure;

FIG. 1B is a sectional view of the inhaler of FIG. 1A;

FIG. 2 is a top isometric view of the inhaler of FIG. 1A with a cap of the inhaler removed;

FIG. 3 is a top isometric view of the inhaler of FIG. 1A with the cap and the pre-metered dose magazine removed to reveal a de-agglomerator of the inhaler including a cover and a base;

FIG. 4 is a top isometric view of the base of the inhaler of FIG. 1A;

FIG. 5 is an exploded, bottom isometric view of the inhaler of FIG. 1A;

FIG. 6 is an enlarged bottom plan view of a portion of the cap of the inhaler of FIG. 1A;

DESCRIPTION OF THE PREFERRED EMBODIMENT

Figure 7:
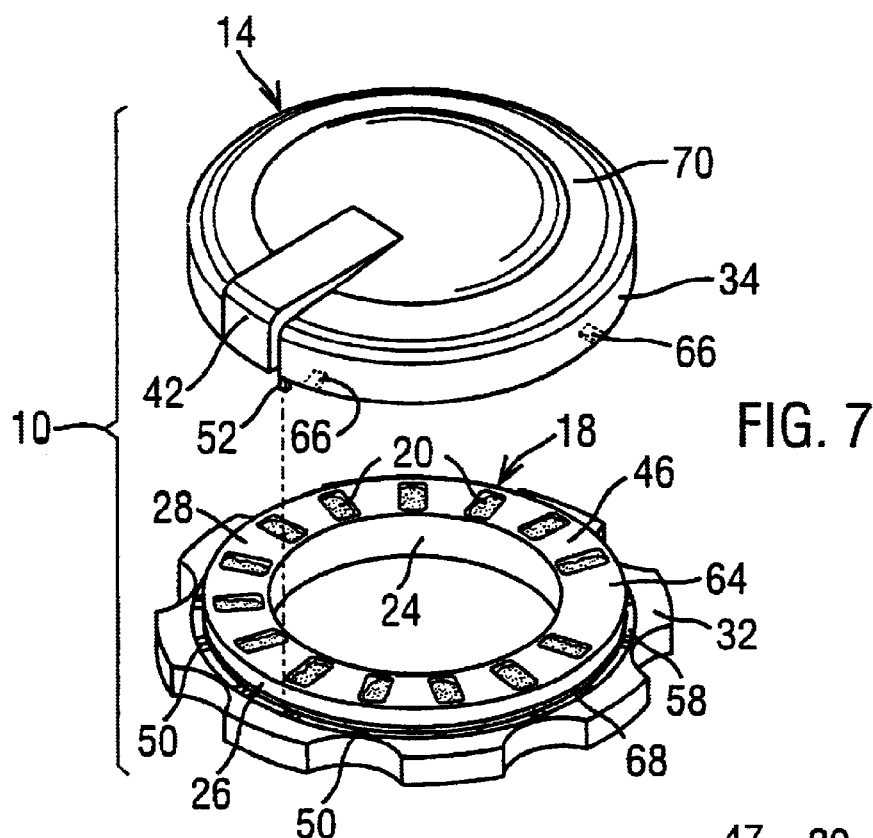
FIG. 7 is an exploded, top isometric view of the cap and the pre-metered dose magazine of the inhaler of FIG. 1A.

FIGS. 1A, 1B, 5 and 9 show a preferred embodiment of a pre-metered dose assembly 10 in a dry powder inhaler and, in particular, a breath-actuated, dry powder inhaler 12, all in accordance with the present disclosure. The pre-metered dose assembly 10 consistently furnishes precise doses of dry powder, e.g., a dry powder medicament or medicament composition, for inhalation by a patient using the dry powder inhaler 12.

The inhaler 12 generally includes the assembly 10, a swirl chamber 114 extending along axis A, a dry powder supply port 122 in a first end 118 of the swirl chamber, and an outlet port 132 at a second end 120 of the swirl chamber. The assembly 10 includes a cap 14 defining a dry powder delivery passageway 16 for providing air to the dry powder supply port 112 of the swirl chamber 114, and a magazine 18 including a plurality of reservoirs 20 for holding pre-metered doses of dry powder.

During operation, one of the magazine 18 and the cap 14 is movable with respect to the other of the magazine and the cap for sequentially positioning the reservoirs 20 of the magazine 18 within the delivery passageway 16 of the cap 14. Then, a breath-induced low pressure at the outlet port 132 of the swirl chamber 114 of the inhaler 12 causes an air flow, as indicated by arrow 1 in FIG. 9, through the dry powder delivery passageway 16 into the dry powder supply port 122 of the swirl chamber 114. As shown best in FIGS. 5, 6 and 9, the passageway 16 of the cap 14 includes a venturi 22 (or venturi-type restriction) that causes the velocity of the breath-induced air flow to increase. The air pressure in the venturi 22 decreases as a result of the increased velocity, and the drop in pressure causes the pre-metered dose of dry powder to be dragged, or entrained into the air flow traveling to the swirl chamber 114.

Preferably, the magazine 18 is movable with respect to the cap 14 for sequentially positioning the dry powder reservoirs 20 of the magazine 18 within the delivery passageway 16 of the cap 14. However, it should be understood that the magazine 18 could be made stationary, and the cap 14 made moveable with respect to the magazine 18 for sequentially positioning the passageway 16 over the reservoirs 20.

As shown in FIGS. 1A, 1B, 2, 5, 7 and 9, the magazine 18 is provided with an annular shape such that rotation of the annular magazine 18 sequentially positions the plurality of the dry powder reservoirs 20 within the delivery passageway 16 of the cap 14. However, it should be understood that the magazine 18 could be provided in other, suitable shapes and the cap 14 suitably adapted. For example, the magazine 18 could be provided with a straight elongated shape, such that movement of the magazine in the direction of elongation sequentially positions the reservoirs 20 within the delivery passageway 16 of the cap 14.

In particular, the annular magazine 18 includes inner and outer circumferential surfaces 24, 26, and flat top and bottom annular surfaces 28, 30. The magazine 18 also includes a dial 32 radially extending outwardly from the outer circumferential surface 26 for allowing a patient to grip and rotate the magazine 18. The dry powder reservoirs 20 are provided in the top surface 28 of the magazine 18 and are uniformly sized and spaced with respect to one another, as shown best in FIGS. 2 and 7.

As shown in FIGS. 1A, 1B, 5, 7 and 9, the cap 14 is circular and includes a cylindrical side wall 34 received on the outer circumferential surface 26 of the magazine 18, and a flat, bottom annular surface 36 received over the annular top surface 28 of the magazine 18. The magazine 18 and the cap 14, therefore, are adapted for rotation of the magazine 18 within the cap 14. As shown best in FIGS. 5, 6 and 9, the bottom surface 36 of the cap 14 defines the dry powder delivery passageway 16, which extends radially inwardly from a first end 38 at the side wall 34 of the cap 14, to a second end 40 at an inner circumference of the annular bottom surface 36 of the cap 14. The cap 14 also includes a first hood 42 extending downward from the first end 38 of the delivery passageway 16, and creating an air inlet port to the passageway 16 between the cap 14 and the magazine 18. A second hood 44 extends downward from the second end 40 of the delivery passageway 16, into the central void of the annular magazine 18.

The assembly 10 preferably includes a seal for sealing the doses of dry powder in the reservoirs 20 of the magazine 18 in an airtight manner prior to the reservoirs 20 being positioned within the delivery passageway 16 of the cap 14. As shown best in FIGS. 7 and 9, the seal comprises a thin plastic film 46 secured to the annular top surface 28 of the magazine 18 and covering the dry powder in the reservoirs 20 in an airtight manner. The cap 14 includes means for piercing the film 46 above each of the reservoirs 20 prior to the reservoirs 20 being positioned within the delivery passageway 16 of the cap 14. As shown best in FIGS. 5 and 6, the means for piercing comprises a small barb 48 extending downward from the annular bottom surface 36 of the cap 14 in front of the venturi 22 of the delivery passageway 16 (assuming a counter-clockwise rotation of the magazine 18 with respect to the cap 14).

It is intended that a manufacturer will fill the reservoirs 20 of the magazine 18 with properly metered individual doses of dry powder medicament, or medicament composition including medicament and a suitable particulate carrier such as lactose. The filled reservoirs 20 are then sealed in an airtight manner, with the film 46 for example, and the magazine 18 and the cap 14 are provided as an assembly 10 to patients for use with a breath actuated, dry powder inhaler. The pre-metered dose assembly 10 may be provided as part of a disposable inhaler. Alternatively, the dose assembly 10 may be removably insertable into a non-disposable inhaler so that an empty assembly can be replaced by a full assembly.

Figure 7A:
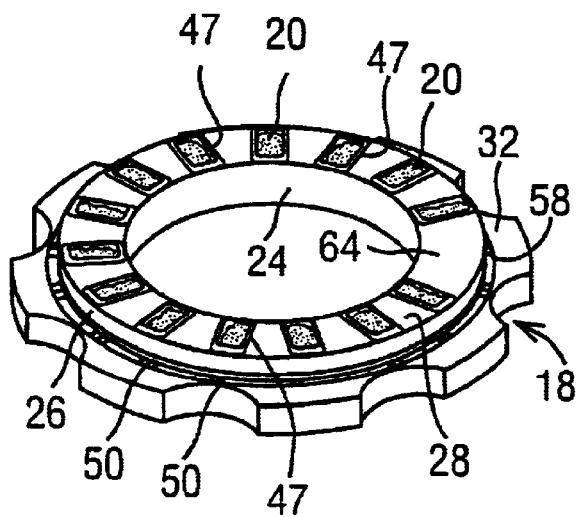
FIG. 7a is a top isometric view of an alternative pre-metered dose magazine for use with the inhaler of FIG. 1A.

Referring to FIG. 7A, a seal for sealing the doses of dry powder in the reservoirs 20 in an airtight manner can alternatively comprise continuous seals 47 surrounding each reservoir on the top surface 28 of the magazine 18. Each seal 47 is made from a soft resilient material, such as a synthetic rubber, and is raised slightly above the level of the top surface 28 of the magazine 18 so that the seal 47 is compressed between the bottom surface 30 of the cap 14 and the top surface 28 of the magazine 18. The compressed seals 47 retain the dry powder in the reservoirs 20 in an airtight manner prior to the reservoirs being moved into the delivery passageway 16. Means for piercing are not required. Preferably, the seals 47 are formed with the magazine 18 in a two step injection molding process.

Preferably, the magazine 18 and the cap 14 are movable with respect to each other through a plurality of discrete increments, wherein at each increment one of the plurality of the dry powder reservoirs 20 of the magazine 18 is positioned within the delivery passageway 16 of the cap 14. In addition, the magazine 18 and the cap 14 are preferably movable in a single direction only with respect to each other, so that a user can access the reservoirs in sequence, without being able to access one of the reservoirs more than once. Furthermore, movement between the magazine 18 and the cap 14 is preferably prevented after all the dry powder reservoirs 20 of the magazine 18 have been positioned in the delivery passageway 16 of the cover, to provide an indication to a patient that all of the doses of the magazine 18 have been used.

Figure 8:
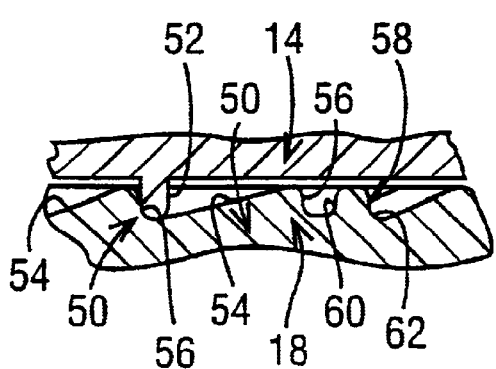
FIG. 8 is a sectional view of portions of the cap and the pre-metered dose magazine of the inhaler of FIG. 1A.
Figure 9:
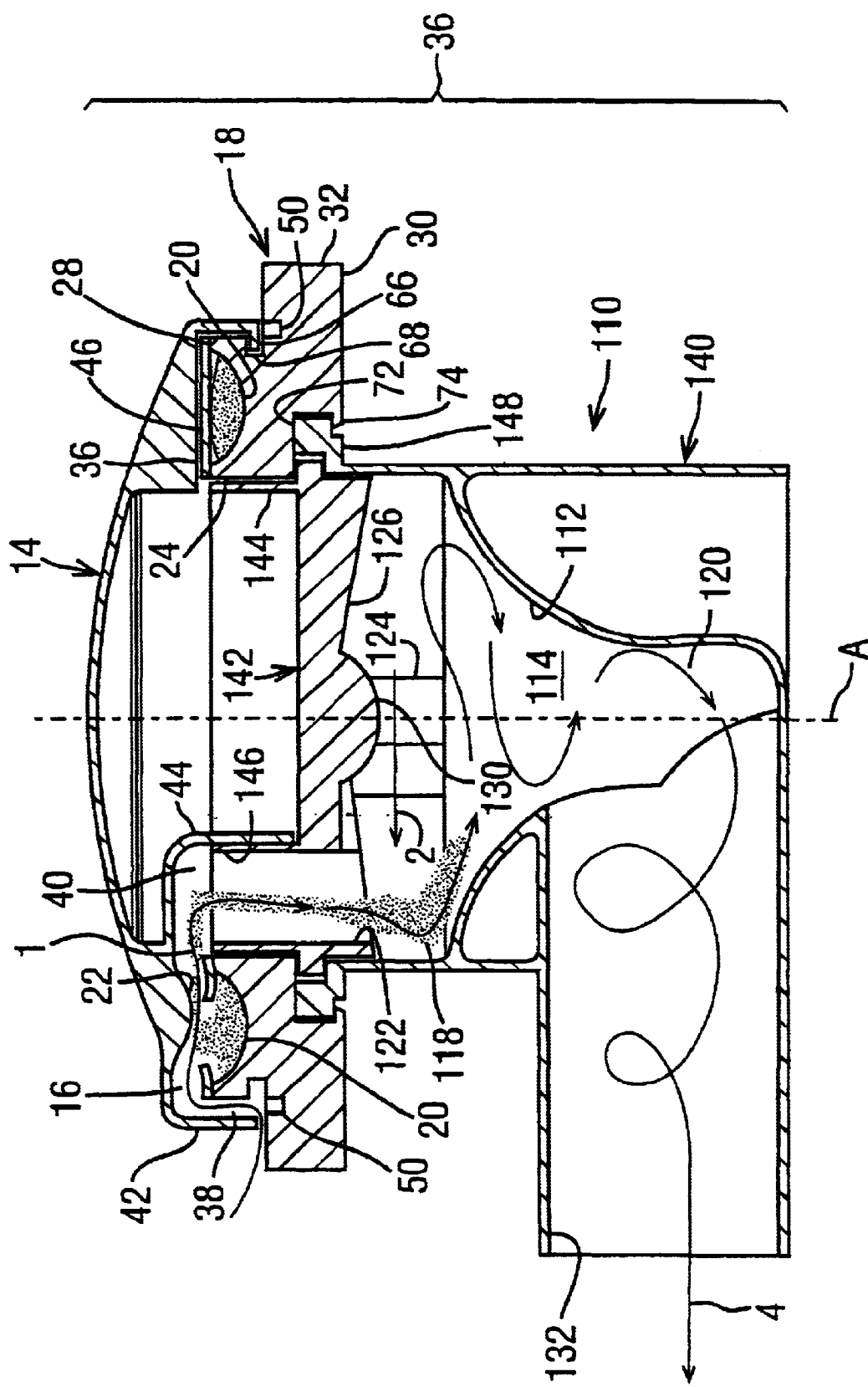
FIG. 9 is a sectional view of the inhaler of FIG. 1A illustrating operation of the inhaler.

As shown best in FIGS. 7 and 8, one of the magazine 18 and the cap 14 includes a plurality of teeth 50, and the other of the magazine 18 and the cap 14 includes a resilient pawl 52 sequentially passing over the teeth during movement of the magazine 18 with respect to the cap 14. When the pawl 52 is between two of the teeth 50, a reservoir 20 of the magazine 18 corresponding to the two teeth is positioned in the delivery passageway 16 of the cap 14. Each of the plurality of teeth 50 has a sloped first side 54 allowing passage of the pawl 52 in only a first direction, and a straight second side 56 preventing passage of the pawl in a second direction. Accordingly, as shown, the magazine 18 can only be rotated in a counter-clockwise direction with respect to the cap 14. In addition, one tooth 58 has straight first and second sides 60, 62 that prevent passage of the pawl 52 past the tooth 58 in any direction. The "last" tooth 58 is positioned to correspond with an empty portion 64 of the top surface 28 of the magazine 18 to prevent movement between the magazine 18 and the cap 14 after all the reservoirs 20 of the magazine 18 have been rotated through the delivery passageway 16.

The assembly 10 also includes a coupler for securing the cap 14 to the magazine 18. As shown best in FIGS. 5 and 9, the coupler comprises resilient tangs 66 extending radially inward from a bottom edge of the side wall 34 of the cap 14 and engaging a circumferential groove 68 of the outer circumferential surface 26 of the magazine 18. The tangs 66 and the groove 68 prevent the cap 14 from being lifted off the magazine 18, yet allow the magazine 18 to rotate with respect to the cap 14.

The assembly 10 additionally includes an indicator for indicating the number of dry powder reservoirs 20 containing dry powder, i.e., the number of pre-metered doses remaining in the magazine 18. As shown in FIGS. 1, 5 and 7, the indicator comprises an annular transparent portion 70 of the cap 14, which allows the reservoirs 20 of the magazine 18 to be viewed through the cap 14 for a determination of how many of the reservoirs 20 contain medicament. Other suitable indicators could alternatively be provided. For example, sequential printed numbers corresponding to the reservoirs 20 of the magazine 18 can be provided on the dial 32 of the magazine 18, so that the number of reservoirs 20 that have passed through the delivery passageway 16 of the cap 14 can be determined by reference to the printed numbers.

Referring to FIGS. 1A through 4 and FIG. 9, the inhaler preferably includes both the presently disclosed pre-metered dose assembly and a de-agglomerator 110. The de-agglomerator 110 is disclosed in co-pending provisional U.S. patent application Ser. No. 60/213,382, filed Jun. 23, 2000 (entitled "De-Agglomerator for Breath-Actuated Dry Powder Inhaler"). The co-pending application is assigned to the assignee of the present disclosure and has been incorporated herein by reference. As its name implies, the de-agglomerator 110 breaks down agglomerates of dry powder before inhalation of the dry powder by a patient.

In general, the de-agglomerator 110 includes an inner wall 112 defining the swirl chamber 114 extending along the axis A from the first end 118 to the second end 120 of the chamber. The swirl chamber 114 includes circular cross-sectional areas arranged transverse to the axis A, which decrease from the first end 118 to the second end 120 of the swirl chamber 114. Preferably, the cross-sectional areas of the swirl chamber 114 decrease monotonically such that any air flow traveling from the first end 118 of the swirl chamber 114 to the second end 120 will at least in part collide with the inner wall 112 of the chamber. In addition, as shown best in FIGS. 1B and 9, the sidewall is preferably convex, i.e., arches inwardly towards the axis A.

Preferably, the dry powder supply port 122 of the de-agglomerator 110 faces in a direction substantially parallel with the axis A of the chamber 114. Accordingly, as shown in FIG. 9, the air flow 1 entering the chamber 114 through the supply port 122 is at least initially directed parallel with respect to the axis A of the chamber.

Referring to FIGS. 1B, 3, 4, 5 and 9, the de-agglomerator 110 additionally includes at least one inlet port 124 in the inner wall 112 of the swirl chamber 114 adjacent to the first end 118 of the chamber providing fluid communication between a region exterior to the de-agglomerator and the first end 118 of the swirl chamber 114. Preferably, the at least one inlet port comprises two diametrically opposed inlet ports 124, 125 that extend in a direction substantially transverse to the axis A and substantially tangential to the circular cross-section of the swirl chamber 114. As a result, air flows, illustrated by arrows 2 and 3 in FIGS. 4 and 9, entering the chamber 114 through the inlet ports 124, 125 are at least initially directed transverse with respect to the axis A of the chamber and collide with the air flow 1 entering through the supply port 122 to create a combined turbulence air flow illustrated by arrow 4.

Referring to FIGS. 1B, 5 and 9, the de-agglomerator 110 includes vanes 126 at the first end 118 of the swirl chamber 114 extending at least in part radially outwardly from the axis A of the chamber. Each of the vanes 126 has an oblique surface 128 facing at least in part in a direction transverse to the axis A of the chamber. The vanes 126 are sized such that at least a portion of the combined air flows 4 collide with the oblique surfaces 128. Preferably, the vanes comprise four vanes 126, each extending between a hub 130 aligned with the axis A and the wall 112 of the swirl chamber 114.

Referring to FIG. 9, the geometry of the swirl chamber 114 causes the combined air flows 4 and the entrained dry powder to follow a turbulent spiral path, or vortex, through the chamber. As will be appreciated, the decreasing cross-sections of the swirl chamber 114 continuously changes the direction and increases the velocity of the spiraling combined air flow 4 and entrained dry powder. Thus, particles and any agglomerates of the dry powder constantly impact against the wall 112 of the swirl chamber 114 and collide with each other, resulting in a mutual grinding or shattering action between the particles and agglomerates. In addition, particles and agglomerates deflected off the oblique surfaces 128 of the vanes 126 cause further impacts and collisions. The constant impacts and collisions cause any agglomerates of dry powder to break into additional particles, and cause the particles to be substantially micronized.

Upon exiting the swirl chamber 114, the direction of the combined air flow 14 and the entrained dry powder is again changed to a transverse direction with respect to the axis A, through the outlet port 132. The combined air flow 4 and the entrained dry powder retain a swirl component of the flow, such that the air flow 4 and the entrained dry powder spirally swirls through the outlet port 132. Since the micronized powder and any remaining agglomerates maintain the swirl imparted from swirl chamber 114, the swirling flow causes additional impacts in the outlet port 132 so as to result in further breaking up of any remaining agglomerates prior to being inhaled by a patient. The de-agglomerator 110, therefore, ensures that particles of the dry powder are small enough for adequate penetration of the powder into a bronchial region of a patient's lungs during inhalation.

As shown best in FIGS. 1B, 3, 4, 5 and 9, the de-agglomerator 110 is preferably assembly from two pieces: a cup-like base 140 and a cover 142. The base 140 and the cover 142 are connected to form the swirl chamber 114. The cup-like base 140 includes the wall 112 and the second end 120 of the chamber and defines the outlet port 132. The base 140 also includes the inlet ports of the swirl chamber 114. The cover 142 forms the vanes 126 and defines the supply port 122.

As shown best in FIGS. 1B, 2, 3, 5 and 9, the cover 142 includes an upwardly extending cylindrical guide 144, and a chimney 146 extending upwardly from the supply port 122 within the guide. The inner circumference 24 of the annular magazine 18 is received coaxially on the guide 144, such that the magazine can be rotated about the guide. The bottom surface 30 of the magazine 18 includes an annular recess 72 receiving a rim 148 of the base 140. The second hood 44 of the cap 14 is received over the chimney 146 of the supply port 122 to connect the delivery passageway 16 of the cap 14 with the supply port 122 of the de-agglomerator 110. In addition, the inhaler 12 includes a coupler for securing the pre-metered dose assembly 10 to the de-agglomerator 110, such that the magazine 18 is free to be rotated with respect to the de-agglomerator. As shown best in FIGS. 1B, 5 and 9, the coupler comprises resilient tangs 74 of the magazine 18 engaging a bottom surface of the rim 148 of the base 140, preventing the assembly 10 from being lifted off the de-agglomerator 110 yet allowing the magazine 18 to rotate.

The base 140, the cover 142, the magazine 18 and the cap 14 are preferably manufactured from a plastic such as polypropylene, acetal or moulded polystyrene, but may be manufactured from metal or another suitable material. Preferably, the cover 142 includes an anti-static additive, such that the dry powder will not cling to the vanes 126. The base 140 and the cover 142 are connected in a manner that provides an air tight seal between the parts. For this purpose heat or cold sealing, laser welding or ultrasonic welding could be used, for example.

Figure 10:
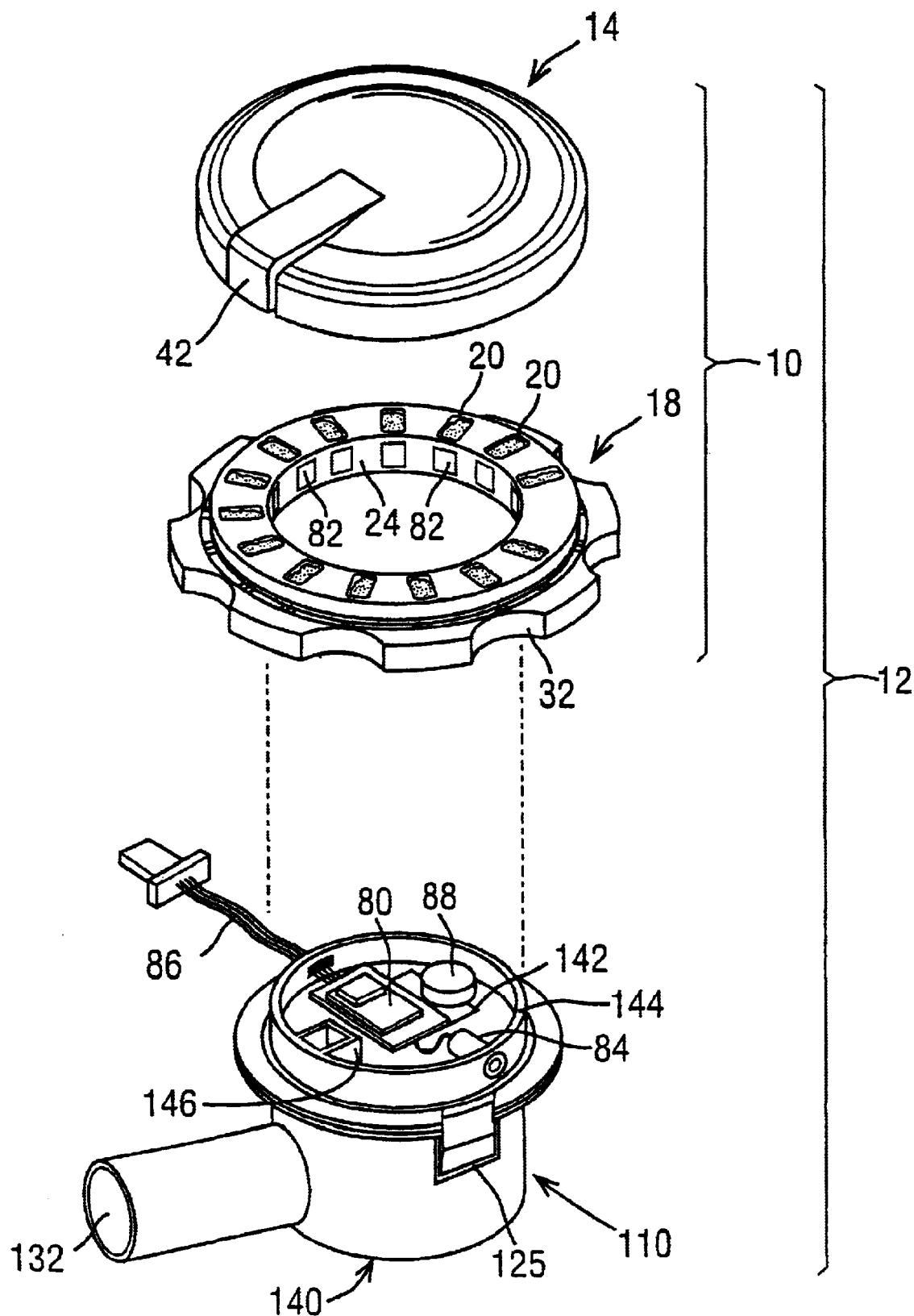
FIG. 10 is an exploded, top isometric view of an additional breath-actuated, dry powder inhaler according to the present disclosure.

Referring now to FIG. 10, an inhaler 12 according to the present disclosure can be provided with a processor 80 for recording how many doses are inhaled from the inhaler by a patient, and at what time the doses are inhaled. The inhaler 12 includes indicators 82 attached to the magazine 18 corresponding to the dry powder reservoirs 20, and a detector 84 mounted on the de-agglomerator 110. The detector 84 provides a signal when one of the indicators 82 passes the detector as the magazine 18 is rotated with respect to the de-agglomerator 110. A signal from the detector 84, therefore, is indicative of a single dose of dry powder being inhaled by a patient through the inhaler 12. The indicators can comprise, for example, reflective strips, while the detector can comprise an LED for directing light on passing reflective strip and a receiver for receiving the reflected light.

Although not shown, a counter provides a sum of the number of signals provided by the detector, while a clock provides a chronological time for each signal provided by the detector. The processor 80 then provides predetermined calculations based upon the sum provided by the counter and the chronological times provided by the clock. The calculations might comprise, for example, the number of doses inhaled by a patient over a day, week or month. A memory stores the calculations provided by the processor 80, and the inhaler 12 further includes a transmitter 86 for transmitting the stored calculations to a remote device for utilizing the calculations. The transmitter might comprise a cable 86 for connection to a doctor's computer upon a patient's visit to the doctor's office, for example. The inhaler 12 includes a battery 88 for powering the detector 84 and the processor 80.

It should be understood that the foregoing detailed description and preferred embodiment is only illustrative of a breath-actuated dry powder inhaler 12 according to the present disclosure. Various alternatives and modifications to the presently disclosed inhaler 12 can be devised by those skilled in the art without departing from the spirit and scope of the present disclosure. For example, the pre-metered dose assembly 10 can be modified for with any inhaler and, in particular, any breath-actuated dry powder inhaler. Accordingly, the present disclosure is intended to embrace all such alternatives and modifications that fall within the spirit and scope of the appended claims.

What is claimed is:

1. A pre-metered dose assembly for use with a breath-actuated dry powder inhaler, comprising:

a cap defining a dry powder delivery passageway for providing air to a dry powder supply port of a chamber of a breath-actuated dry powder inhaler; and a rigid unitary structure magazine including a plurality of integral reservoirs for holding pre-metered doses of dry powder, one of the magazine and the cap movable with respect to the other of the magazine and the cap for sequentially positioning the reservoirs to be adjacent to the delivery passageway of the cap;

whereby a breath-induced low pressure in the chamber of the inhaler causes an air flow through the dry powder delivery passageway and into the dry powder supply port, and the air flow entrains dry powder from the dry powder reservoir positioned in the passageway into the chamber for inhalation by a patient using the inhaler; and a unitary structure means sealing each of the reservoirs of the magazine in a substantially airtight manner prior to the reservoir being positioned within the delivery passageway of the cap, and maintaining said reservoirs unsealed otherwise.

2. An assembly according to claim 1, wherein the magazine is movable with respect to the cap for sequentially positioning the plurality of the dry powder reservoirs within the delivery passageway of the cap.

3. An assembly according to claim 2, wherein the magazine is annular such that rotation of the annular magazine sequentially positions the plurality of the dry powder reservoirs within the delivery passageway of the cap.

4. An assembly according to claim 1, further including means for indicating the number of dry powder reservoirs containing dry powder.

5. An assembly according to claim 4, wherein the cap covers the plurality of the dry powder reservoirs of the magazine and the means for indicating comprises a transparent portion of the cap.

6. An assembly according to claim 1, wherein one of the magazine and the cap is movable with respect to the other of the magazine and the cap through a plurality of discrete increments, wherein at each increment one of the plurality of the dry powder reservoirs is positioned within the delivery passageway of the cap.

7. An assembly according to claim 1, wherein one of the magazine and the cap is movable with respect to the other of the magazine and the cap in only a single direction.

8. An assembly according to claim 1, adapted such that the magazine and the cap will be unmovable with respect to each other after all of the dry powder reservoirs of the magazine have been positioned in the dry powder delivery passageway of the cover.

9. An assembly according to claim 1, wherein:
one of the magazine and the cap includes a plurality of teeth; and
the other of the magazine and the cap includes a resilient pawl sequentially passing over the teeth during movement of one of the magazine and the cap with respect to the other of the magazine and the cap, wherein the magazine is in one of the plurality of discrete increments when the pawl is between teeth.

10. An assembly according to claim 9, wherein each of the plurality of teeth has a sloped first side allowing passage of the pawl in a first direction, and a straight second side preventing passage of the pawl in a second direction.

11. An assembly according to claim 9, wherein the plurality of teeth includes one tooth having straight first and second sides preventing passage of the pawl past said one tooth.

12. An assembly according to claim 1, further comprising dry powder contained in the reservoirs of the magazine.

13. An assembly according to claim 12, wherein each reservoir of the magazine contains a single dose of the dry powder.

14. An assembly according to claim 13, wherein the dry powder comprises a medicament composition having at least one active agent medicament adhered to a particulate carrier.

15. An assembly according to claim 1, wherein the unitary structure means for sealing comprises a film secured to the magazine and covering the reservoirs in a substantially airtight manner.

16. A pre-metered dose assembly, comprising:

a cap defining a delivery passageway;

a rigid unitary structure magazine including a plurality of integral reservoirs, one of the magazine and the cap movable with respect to the other of the magazine and the cap for sequentially positioning the reservoirs to be adjacent to the delivery passageway of the cap;

doses of dry powder contained in the reservoirs of the magazine;

a film secured to the magazine and covering the dry powder in the reservoirs in a substantially airtight manner; and the cap includes means for piercing the film above each of the reservoirs prior to the reservoir being positioned within the delivery passageway of the cap.

17. An assembly according to claim 16, wherein the dry powder delivery passageway of the cap includes a venturi.

18. An assembly according to claim 1, wherein the dry powder delivery passageway of the cap includes a venturi.

19. An assembly according to claim 1, wherein:

the magazine is annular such that rotation of one of the magazine and the cap with respect to the other of the magazine and the cap sequentially positions the plurality of the dry powder reservoirs within the delivery passageway of the cap, the magazine having a top surface defining the reservoirs; and the cap includes a lower surface received over the top surface of the magazine, the lower surface defining the dry powder delivery passageway extending radially inwardly from an outer portion to an inner portion of the cap.

20. An assembly according to claim 1, further comprising means for securing the cap to the magazine.

21. An assembly according to claim 1, further comprising means for securing the assembly to a chamber of an inhaler.

22. A breath-actuated dry powder inhaler including an assembly according to claim 1, and further comprising:

a chamber extending along an axis between a first end and a second end;

a dry powder supply port in the first end of the chamber in fluid communication with the dry powder delivery port of the cap; and an outlet port at a second end of the chamber;

whereby a breath-induced low pressure at the outlet port causes air flow into the chamber through the dry powder supply port, with the air flow through the dry powder supply port entraining dry powder into the chamber from the reservoir of the magazine positioned in the delivery passageway.

23. An inhaler according to claim 22, further comprising a de-agglomerator having:

an inner wall defining the chamber extending along an axis from a first end to a second end;

at least one inlet port in the inner wall adjacent to the first end of the chamber providing fluid communication between a region exterior to the de-agglomerator and the first end of the chamber;

whereby a breath-induced low pressure at the outlet port also causes an air flow into the chamber through the inlet port.

24. An inhaler according to claim 23, wherein the de-agglomerator further comprises vanes at the first end of the chamber extending at least in part radially outwardly from the axis of the chamber, each of the vanes having an oblique surface facing at least in part in a direction transverse to the axis.

25. An inhaler according to claim 24, wherein the chamber of the de-agglomerator includes cross-sectional areas arranged transverse to the axis, the cross-sectional areas decreasing monotonically from the first end to the second end of the chamber.

26. An inhaler comprising:

a cap defining a dry powder delivery passageway;

a magazine including a plurality of reservoirs for holding pre-metered doses of dry powder, one of the magazine and the cap movable with respect to the other of the magazine and the cap for sequentially positioning the reservoirs within the delivery passageway of the cap;

a chamber having an inner wall extending along an axis between a first end attached to the cap and the magazine and a second end, and cross-sectional areas arranged transverse to the axis and decreasing monotonically from the first end to the second end of the chamber;

a dry powder supply port in the first end of the chamber in fluid communication with the dry powder delivery port of the cap, wherein the dry powder supply port faces in a direction substantially parallel to the axis;

an outlet port at a second end of the chamber, wherein the outlet port extends substantially transverse to the axis;

vanes at the first end of the chamber extending at least in part radially outwardly from the axis of the chamber, each of the vanes having an oblique surface facing at least in part in a direction transverse to the axis; and at least one inlet port in the inner wall adjacent to the first end of the chamber providing fluid communication between a region exterior to the inhaler and the first end of the chamber, wherein the at least one inlet port extends in a direction substantially transverse to the axis and substantially tangential to the chamber.

27. An inhaler according to claim 26, wherein the at least one inlet port of the de-agglomerator comprises two diametrically opposed inlet ports.

28. An inhaler according to claim 27, wherein:

the de-agglomerator comprises a cup-like base closed with a cover to form the chamber, the base defining the inner wall, and the second end of the chamber and the outlet port, the cover defining the first end of the chamber, the vanes and the supply port, and the base and the cover in combination defining the at least one inlet port, the cover including a cylindrical guide extending upwardly from the chamber and a chimney extending upwardly within the cylindrical guide from the supply port;

the magazine is annular and has an inner circumferential surface received coaxially on the cylindrical guide of the de-agglomerator for rotation of the magazine with respect to the de-agglomerator, the magazine having a top surface defining the dry powder reservoirs; and the cap includes a lower surface received over the top surface of the magazine, the lower surface defining the dry powder delivery passageway extending radially inwardly from from an outer portion to an inner portion of the cap, the cap further including a hood extending downwardly from the inner portion and received over the chimney of the de-agglomerator, the hood connecting the delivery passageway to the chimney and preventing rotation of the cap with respect to the de-agglomerator.

29. An inhaler according to claim 28, further comprising:

indicators attached to the magazine corresponding to the dry powder reservoirs; and a detector mounted on the de-agglomerator providing a dose signal upon an indicator passing the detector as the magazine is moved with respect to the de-agglomerator to position one of the reservoirs in the dry powder delivery passageway, whereby a dose signal from the detector is indicative of the dispensing of a single reservoir of dry powder through the inhaler.

30. An inhaler according to claim 29, further comprising:

a counter providing a sum of the number of dose signals provided by the detector;

a clock for providing a time for each dose signal provided by the detector;

a processor for providing predetermined calculations based upon the sum provided by the counter and the times provided by the clock;

memory for storing the calculations provided by the processor; and means for transmitting the stored calculations to a remote device for utilizing the calculations.

31. A method of providing pre-metered doses of dry powder for patient inhalation through a breath-actuated dry powder inhaler including a chamber extending along an axis from a first end to a second end, a dry powder supply port in the first end of the chamber, and an outlet port at the second end of the chamber, the method comprising:

pre-metering a plurality of doses of dry powder;

defining a dry powder delivery passageway for providing air to the dry powder supply port of the chamber;

positioning at least one of the pre-metered doses of dry powder within the delivery passageway;

inducing a low pressure at the outlet port of the chamber of the inhaler through patient inhalation to create an air flow through the dry powder delivery passageway, the dry powder supply port, the chamber, and the outlet port and into the patient's lungs; and restricting the air flow through the delivery passageway so that the air flow entrains the pre-metered dose of dry powder;

directing the breath-actuated air flow entraining the pre-metered dose of dry powder through the supply port in a substantially longitudinal direction into the first end of the chamber with respect to the axis of the chamber;

directing a second breath-actuated air flow in a substantially transverse direction into the first end of the chamber with respect to the axis of the chamber such that the second air flow collides and substantially combines with the entraining air flow;

deflecting a portion of the combined air flows in a substantially axial direction towards the second end of the chamber;

directing the remaining portion of the combined air flows in a substantially spiral path towards the second end of the chamber; and directing all the combined air flows from the second end of the chamber through the outlet port in a substantially transverse direction with respect to the axis of the chamber.

32. A method according to claim 31, further comprising:

sealing the pre-metered doses in an airtight manner; and unsealing the at least one pre-metered dose in the dry powder delivery passageway prior to inducing a low pressure at the outlet port of the inhaler.

33. A method according to claim 31, further comprising: indicating the number of pre-metered doses entrained through the delivery passageway.

34. A method according to claim 31, further comprising:

indicating a sum of the doses entrained through the delivery passageway;

indicating chronological times of when the doses were entrained through the delivery passageway;

providing predetermined calculations based upon the indicated sum and times; and storing the calculations.

35. A method according to claim 31, wherein the second breath-actuated air flow is also directed tangentially into the first end of the chamber.

36. A method according to claim 35, wherein a third breath-actuated air flow is directed in a substantially transverse direction into the first end of the chamber with respect to the axis of the chamber such that the third air flow collides and substantially combines with the entraining air flow and the second air flow.

37. A method according to claim 35, wherein the combined air flows are constricted between the first end and the second end of the chamber.

38. A method of providing pre-metered doses of dry powder for patient inhalation through a breath-actuated dry powder inhaler including a chamber extending along an axis from a first end to a second end, a dry powder supply port in the first end of the chamber, and an outlet port at the second end of the chamber, the method comprising:

defining a dry powder delivery passageway for providing air to the dry powder supply port of the chamber of the breath-actuated dry powder inhaler; and providing a rigid unitary structure magazine including a plurality of integral reservoirs;

pre-metering at least one dose of dry powder within each reservoir of the magazine;

moving the magazine with respect to the dry powder delivery passageway to sequentially position one of the reservoirs within the delivery passageway;

inducing a low pressure at the outlet port of the chamber of the inhaler through patient inhalation to create an air flow through the dry powder delivery passageway, the dry powder supply port, the chamber, and the outlet port and into the patient's lungs; and restricting the air flow through the delivery passageway so that the air flow entrains the at least one pre-metered dose of dry powder from the reservoir positioned in the passageway; and sealing the pre-metered doses in an airtight maimer within the reservoirs of the magazine using a film.

39. A method according to claim 38, wherein the film is provided as a plastic film.

40. A method according to claim 39, further comprising:

unsealing a portion of the film above the reservoir positioned in the dry outlet powder delivery passageway prior to inducing a low pressure at the outlet port of the inhaler.

41. A breath-actuated dry powder inhaler comprising:

a pre-metered dose assembly including a cap defining a delivery passageway, and a magazine including a plurality of reservoirs, and wherein one of the magazine and the cap is movable with respect to the other of the magazine and the cap for sequentially positioning the reservoirs within the delivery passageway of the cap; and a de-agglomerator including, an inner wall defining a chamber extending along an axis from a first end to a second end having an outlet port, wherein the chamber of the de-agglomerator includes cross-sectional areas arranged transverse to the axis and decreasing monotonically from the first end to the second end of the chamber, a dry powder supply port in the first end of the chamber facing in a direction substantially parallel to the axis, and in fluid communication with the dry powder delivery port of the cap, an outlet port at a second end of the chamber extending substantially transverse to the axis, at least one inlet port in the inner wall adjacent to the first end of the chamber and extending substantially transverse to the axis and substantially tangential to the chamber, and vanes at the first end of the chamber extending at least in part radially outwardly from the axis of the chamber, each of the vanes having an oblique surface facing at least in part in a direction transverse to the axis.

42. An inhaler according to claim 41, wherein the at least one inlet port of the de-agglomerator comprises two diametrically opposed inlet ports.

43. An inhaler according to claim 42, wherein:

the de-agglomerator comprises a cup-like base closed with a cover to form the chamber, the base defining the inner wall, and the second end of the chamber and the outlet port, the cover defining the first end of the chamber, the vanes and the supply port, and the base and the cover in combination defining the at least one inlet port, the cover including a cylindrical guide extending upwardly from the chamber and a chimney extending upwardly within the cylindrical guide from the supply port;

the magazine is annular and has an inner circumferential surface received coaxially on the cylindrical guide of the de-agglomerator for rotation of the magazine with respect to the de-agglomerator, the magazine having a top surface defining the dry powder reservoirs; and the cap includes a lower surface received over the top surface of the magazine, the lower surface defining the dry powder delivery passageway extending radially inwardly from an outer portion to an inner portion of the cap, the cap further including a hood extending downwardly from the inner portion and received over the chimney of the de-agglomerator, the hood connecting the delivery passageway to the chimney and preventing rotation of the cap with respect to the de-agglomerator.

44. An assembly according to claim 41, wherein the magazine is movable with respect to the cap for sequentially positioning the plurality of the dry powder reservoirs within the delivery passageway of the cap.

45. An assembly according to claim 44, wherein the magazine is annular such that rotation of the annular magazine sequentially positions the plurality of the dry powder reservoirs within the delivery passageway of the cap.

46. An assembly according to claim 41, wherein:

one of the magazine and the cap includes a plurality of teeth; and the other of the magazine and the cap includes a resilient pawl sequentially passing over the teeth during movement between the magazine and the cap.

47. An assembly according to claim 46, wherein each of the plurality of teeth has a sloped first side allowing passage of the pawl in a first direction, and a straight second side preventing passage of the pawl in a second direction.

48. An assembly according to claim 46, wherein the plurality of teeth includes one tooth having straight first and second sides preventing passage of the pawl past said one tooth.

49. An assembly according to claim 41, further comprising dry powder contained in the reservoirs of the magazine.

50. An assembly according to claim 49, wherein each reservoir of the magazine contains a single dose of the dry powder.

51. An assembly according to claim 16, wherein the film secured to the magazine and covering the reservoirs in a substantially airtight manner comprises a plastic film.

52. An assembly according to claim 16, wherein the film secured to the magazine and covering the dry powder in the reservoirs in a substantially airtight manner comprises a plastic film.

53. A pre-metered dose assembly, comprising:
   a. cap defining a delivery passageway; and
   a rigid unitary structure magazine including a plurality of integral reservoirs, one of the magazine and the cap movable with respect to the other of the magazine and the cap for sequentially positioning the reservoirs within the delivery passageway of the cap;
   a unitary structure means sealing each of the reservoirs of the magazine in a substantially airtight manner prior the reservoir being positioned within the delivery passageway of the cap, and maintaining said reservoirs unsealed otherwise.

54. An assembly according to claim 53, wherein the unitary structure means for sealing comprises a film secured to the magazine and covering the reservoirs in a substantially airtight manner.

55. An assembly according to claim 54, wherein the film comprises a plastic film.

56. An assembly according to claim 54, wherein the cap includes means for piercing the film above each of the reservoirs prior to the reservoir being positioned within the delivery passageway of the cap.

57. An assembly according to claim 53, wherein the reservoirs are formed in a surface of the magazine and the unitary structure means for sealing comprises a unitary surface of the cap adapted to overlie each of the reservoirs prior to the reservoir being positioned within the delivery passageway of the cap, and continuous, resilient seals positioned on the surface of the magazine around each of the reservoirs, the resilient seals compressed between the overlying surface of the cap and the surface of the magazine.

58. An assembly according to claim 53, further comprising dry powder contained in the reservoirs of the magazine.

59. An assembly according to claim 58, wherein each reservoir of the magazine contains a single dose of the dry powder.

* * * * *

UNITED STATES PATENT AND TRADEMARK OFFICE
CERTIFICATE OF CORRECTION

PATENT NO. : 6,655,381 B2
DATED : December 2, 2003
INVENTOR(S) : Laurence Keane et al.

It is certified that error appears in the above-identified patent and that said Letters Patent is hereby corrected as shown below:

Column 13,
Line 35, after "airtight", delete "maimer" and insert thereof -- manner --;

Column 15,
Line 6, after first "a", delete ".".

Signed and Sealed this

Thirteenth Day of April, 2004

JON W. DUDAS
*Acting Director of the United States Patent and Trademark Office*